US008853257B2

(12) United States Patent
Sharir

(10) Patent No.: US 8,853,257 B2
(45) Date of Patent: Oct. 7, 2014

(54) SUCCINIMIDE DERIVATIVES AS OCULAR HYPOTENSIVE AGENTS

(76) Inventor: Mordechai Sharir, Rishon Lezion (IL)

(*) Notice: Subject to any disclaimer, the term of this patent is extended or adjusted under 35 U.S.C. 154(b) by 92 days.

(21) Appl. No.: 13/226,176

(22) Filed: Sep. 6, 2011

(65) Prior Publication Data

US 2012/0016001 A1 Jan. 19, 2012

Related U.S. Application Data

(63) Continuation-in-part of application No. 12/094,155, filed as application No. PCT/IL2006/001315 on Nov. 14, 2006, now abandoned.

(60) Provisional application No. 60/739,964, filed on Nov. 28, 2005.

(30) Foreign Application Priority Data

Nov. 21, 2005 (IL) .......................... 172070

(51) Int. Cl.
  *A61K 31/4015* (2006.01)
  *A61K 9/00* (2006.01)
  *A61K 9/06* (2006.01)
(52) U.S. Cl.
  CPC ........... *A61K 31/4015* (2013.01); *A61K 9/0048* (2013.01); *A61K 9/0051* (2013.01); *A61K 9/06* (2013.01); *Y10S 514/913* (2013.01)
  USPC .......................................... 514/425; 514/913
(58) Field of Classification Search
  USPC .................................. 514/425, 913
  See application file for complete search history.

(56) References Cited

U.S. PATENT DOCUMENTS

| | | | |
|---|---|---|---|
| 4,188,398 A | 2/1980 | Mndzhoian et al. |
| 4,537,892 A | 8/1985 | York, Jr. |
| 4,598,078 A | 7/1986 | Ishizumi et al. |
| 4,600,717 A | 7/1986 | York, Jr. |
| 4,609,663 A | 9/1986 | York, Jr. |
| 4,665,089 A | 5/1987 | Siezen et al. |
| 4,717,725 A | 1/1988 | York, Jr. |
| 4,792,569 A | 12/1988 | Maryanoff et al. |
| 4,843,078 A | 6/1989 | Ishizumi et al. |
| 4,981,867 A | 1/1991 | Prince |
| 4,981,871 A | 1/1991 | Abelson |
| 5,091,421 A | 2/1992 | Clark et al. |
| 5,153,211 A | 10/1992 | York, Jr. |
| 5,284,874 A | 2/1994 | Clark et al. |
| 5,290,813 A | 3/1994 | Clark et al. |
| 5,338,545 A | 8/1994 | Clark et al. |
| 5,401,880 A | 3/1995 | Clark et al. |
| 5,514,815 A | 5/1996 | Iwasaki et al. |
| 5,658,940 A | 8/1997 | Muller et al. |
| 6,093,820 A | 7/2000 | Gutman et al. |
| 6,165,500 A | 12/2000 | Cevc |
| 6,372,245 B1 | 4/2002 | Bowman et al. |
| 6,541,037 B1 | 4/2003 | Lee et al. |
| 6,949,518 B1 | 9/2005 | Chu et al. |
| D524,942 S | 7/2006 | Felix |
| 2005/0175690 A1 | 8/2005 | Edgren et al. |

FOREIGN PATENT DOCUMENTS

| | | |
|---|---|---|
| EP | 0316438 B1 | 9/1993 |
| WO | 88/09660 A2 | 12/1988 |
| WO | 2005/065646 A2 | 7/2005 |
| WO | 2007/057889 A2 | 5/2007 |

OTHER PUBLICATIONS

Coulter et al., (1989) Characterization of ethosuximide reduction of low-threshold calcium current in thalamic neurons. Ann Neurol 25(6): 582-593.
Huguenard (1999): "Neoronal Circuitry of Thalamocortical Epilepsy and Mechanisms of Anti-absence Drug Action" in Jasper's Basic Mechanism of the Epilepsis, 3rd Ed., Advances in Neurology, vol. 79, Chapter 67, Edited by Delagado-Escueta et al. Lipp, 10 pages.
Moore et al., (1993) Noninvasive measurement of rat intraocular pressure with the Tono-Pen. Invest Ophthalmol Vis Sci 34(2): 363-369.
Pang et al., (2005) Acute effects of glaucoma medications on rat intraocular pressure. Exp Eye Res 80(2): 207-214.
Rankin (2004) Nephrotoxicity induced by C- and N-arylsuccinimides. J Toxicol Environ Health B Crit Rev 7(5): 399-416.
Sharir, M.: "Novel Thiadiazole Sulfonamide Carbonic Anhydrase Inhibitors as Topically Effective Ocular Hypotensive Agents", PhD Thesis, University of Louisville, Louisville, KY, USA, May 1990.
Shields (1998) Textbook of Glaucoma, 4th Ed., Williams & Wilkins, Baltimore.

*Primary Examiner* — Zohreh Fay
(74) *Attorney, Agent, or Firm* — Rothwell, Figg, Ernst & Manbeck, P.C.

(57) ABSTRACT

The present invention provides methods and pharmaceutical compositions for treating ocular disorders associated with elevated intraocular pressure, such as glaucoma, by administering anti-epileptic or anti-convulsant compounds of the succinimide family, in particular compounds of formula I and/or II as defined herein.

17 Claims, No Drawings

SUCCINIMIDE DERIVATIVES AS OCULAR HYPOTENSIVE AGENTS

CROSS-REFERENCE TO RELATED APPLICATIONS

This application is a continuation-in-part of U.S. patent application Ser. No. 12/094,155, filed May 19, 2008, now abandoned which is a 371 filing of International Patent Application PCT/IL06/01315, filed Nov. 14, 2006, which claims the benefit of Application No. 60/739,964, filed on Nov. 28, 2005 and Israel Application No. 172070, filed on Nov. 21, 2005. The contents of each application mentioned above are expressly incorporated by reference herein.

FIELD OF THE INVENTION

The present invention generally relates to treatment of ocular disorders and more specifically to the use of succinimide compounds of formula I and/or II, as well as representative examples of compounds encompassed by such formulae, in topical ophthalmic formulations for treating ocular disorders associated with elevated intraocular pressure, such as glaucomas.

BACKGROUND OF THE INVENTION

Glaucomas are a family of ocular disorders usually characterized by an increased intraocular pressure (IOP) with a typical damage to the optic nerve and the visual field; but many exceptions exist. The level of IOP is the net result of production minus outflow from the eye, via a ring-like sieve structure called the trabecular meshwork, located at the angle of the anterior chamber. While most of the hypertensive glaucomas result from increased trabecular resistance to outflow, most of the medical therapy focuses on decreasing the inflow (See Shields M. B.: Textbook of Glaucoma, 4th Ed., Williams & Wilkins, Baltimore, 1998). Every minute approximately 1.8-4.2 microliter of aqueous humor is produced and secreted into the posterior chamber of the eye by the non-pigmented ciliary epithelium. The process is not well understood, but seems to involve a combination of active ultrafiltration and passive transport. The rate of secretion is influenced by multiple factors, e.g. diurnal curve, pH, age, enzymes like carbonic anhydrase (CA) as well as vascular diseases. Several anti-glaucoma drug classes influence various stages of the aqueous humor flow, e.g. beta-adrenoreceptor antagonists (timolol, betaxolol) systemic and topical carbonic anhydrase (CA) inhibitors (acetazolamide, dorzolamide, See Sharir M.: Novel Thiadiazole Sulfonamide Carbonic Anhydrase Inhibitors as Topically Effective Ocular Hypotensive Agents, PhD Thesis, University of Louisville, Louisville, Ky., USA, May 1990), alpha adrenoreceptor agonists (brimonidine, apraclonidine) and prostaglandin analogues (latanoprost, bimatoprost) to name a few. Most drug groups act synergistically to decrease aqueous humor production and secretion by up to 50% with some 'unconventional' outflow additive effect of the prostaglandins. Studies in aqueous humor dynamics elicited some pivotal components in the secretion processes. While bicarbonate is found in higher than plasma concentration in the posterior chamber of the rabbit (probably a direct result of CA involvement), it is not the case in humans, where chloride has been suggested as the key anion.

The mechanism of fluid secretion across semi-permeable/selective tissue membranes in the human body shares similarities in most organ systems. At some point, in the cell membrane, "water splitting" occurs: the proton follows an anion (to maintain electro-neutrality) and gets to one side while the hydroxyl usually couples with sodium or another positively charged component and ends up in the contralateral side of the cell membrane. The substrate used for this water splitting is carbon dioxide, which gets hydrated to form the (weak) carbonic acid; consequently its proton and bicarbonate are separated by the cell membrane. This process generates passive water secretion, to accompany the electrolytes and maintain both electric and osmotic equilibrium. The reaction is catalyzed by CA.

Aqueous humor is produced and secreted into the posterior chamber of the eye by the non-pigmented ciliary epithelium, similarly to the cerebrospinal fluid (CSF), formed by the choroidal plexus and secreted across the floor of the brain ventricles. A basolateral Chloride/Bicarbonate-anion exchanger switches between the two and it is suggested that succinimides, by way of disrupting first the T-calcium channels and then the anion equilibrium, disrupt aqueous humor production, hence decreasing the intraocular pressure.

The typical absence epilepsy of childhood is a non-convulsive form of epilepsy that is characterized by frequent "absences" and bilaterally synchronous 3/s spike and wave electroencephalographic features, often called 'spike-wave-discharge'(SWD). Absence seizures are idiopathic and are divided according to the age of onset to childhood absence epilepsy (CAE, or pyknolepsy), juvenile absence epilepsy (JAE) and juvenile myoclonic epilepsy (JME or impulsive Petit Mal seizures). All these conditions are associated with the SWD pattern, and seizures that may last from few seconds to minutes, sometimes several hundred attacks per day. The pathogenesis is still unknown. Multiple studies suggest that epilepsy can result from processes which disturb extracellular ion homeostasis, alter energy metabolism, change receptor function or alter transmitter uptake. Recent studies suggest that a reverberant, thalamo-cortical neuronal circuitry underlies the SWD seizures. (See Huguenard J. R.: Neuronal Circuitry of Thalamocortical Epilepsy and Mechanism of Anti-absence Drug Action. In: Jasper's Basic Mechanism of the Epilepsies, 3rd Ed., Advances in Neurology, Vol. 79, Chapter 67, edited by A. V. Delgado-Escueta et. al. Lippincott Williams & Wilkins, Philadelphia, 1999). Ethosuximide and its methsuximide metabolite may exert their action through alteration in thalamic cellular excitability, possibly by blocking the T-type calcium current, while a tetramethyl derivative might cause convulsions (Coulter D. A., Huguenard J. R., Prince D. A.: Characterization of ethosuximide reduction of low-threshold calcium current in thalamic neurons. Ann. Neurol. 1989; 25:582-593.). While T-channel blockade is important, it is not the sole anti-absence drug mechanism. The effectiveness of the benzodiazepine clonazepam in ameliorating absence epilepsy suggested that the GABA receptor system is important as well as a wider network of neuronal system. Other theories suggest that some of the CAE or JAE, especially the hereditary types are because of defects in CLCN-2 (Chloride channel Protein 2).

U.S. Pat. No. 4,981,867 discloses the use of succinimides, including the anti-convulstant and anti-epileptic drugs ethosuximide, methsuximide and phensuximide, for treating for reducing tremor.

U.S. Pat. No. 4,188,398 teaches antiepileptic activity of □-/para-isopropyloxyphenyl/succinimides.

U.S. Pat. No. 4,609,663 teaches a method of treating glaucoma by administering aldose reductase inhibitors including spiro fluoren-, or indeno[1,2]b]pyridine-succinimide derivatives.

U.S. Pat. Publication No. 2005/0175690 discloses oral drug compositions comprising a pharmaceutical agent and a solubilizing agent, wherein the pharmaceutical agent is selected from a low solubility pharmaceutical agent or a low dissolution rate pharmaceutical agent. The low solubility pharmaceutical agent is preferably other than ethosuximide, methsuximide, and phensuximide. U.S. 2005/0175690 does not teach ophthalmic pharmaceutical formulations.

There is an unmet need for new therapies for treating ocular disorders associated with elevated intraocular pressure, such as glaucomas.

SUMMARY OF THE INVENTION

The present invention provides methods and pharmaceutical compositions for treating ocular disorders associated with elevated intraocular pressure, such as glaucoma, which are based on a novel use of ophthalmic compositions comprising anti-epileptic or anti-convulsant compounds of formula I and/or II, as well as representative examples of compounds encompassed by such formulae, as ocular hypotensive agents.

It has now unexpectedly been discovered that anti-epileptic or anti-convulsant agents of the succinimide type, in particular compounds of formula I or II are also effective as anti-glaucoma agents, possibly by disrupting the T-calcium channels and then anion equilibrium, disrupting aqueous humor production, and hence decreasing the intraocular pressure. Without wishing to be bound by any theory regarding the mechanism of action, the present invention is based on the unexpected finding of similarities in the pathophysiology of Petit Mal (Absence) epilepsy and the glaucomas. Both diseases reflect a change in rate of secretion and/or defective outflow facility, which creates a local tissue electrolytic, ionic and osmotic imbalance, producing a characteristic cascade of symptoms.

Glaucoma is characterized by increased intraocular pressure (IOP), where the IOP level is the net result of production minus outflow of aqueous humor from the eye. Thus, it is now proposed for the first time that antiepileptic medications of the succinimide type, and in particular of formula I or II have ocular hypotensive efficacy by modulating the ionic channels, and controlling the rate of production and secretion of the aqueous humor from the non-pigmented ciliary body of the eye. Accordingly, the present invention provides a novel use of succinimide compounds of formula I and/or II, for the treatment of ocular disorders associated with elevated ocular pressure, in particular glaucomas. This novel and unobvious connection between anti-epileptic and anti-glaucoma treatment in general, and by succinimides of formula I or II has not been made prior to the present invention. In fact, there are many types of known anti-convulsant agents (e.g., aldehydes, barbiturates, benzodiazepines, bromides, carbamates, carboxamides, fatty acids and GABA analogs, hydantoins, oxazolidones, propionates, pyrimidine-diones, pyrrolidines and triazines), none of which are known for the treatment of glaucoma or other eye diseases.

According to one aspect of the present invention there is provided a method for treating ocular hypertension by administering to a subject in need of such a treatment an effective amount of an ophthalmic pharmaceutical composition containing a succinimide compound of formula I as the active ingredient:

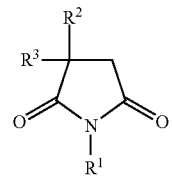

wherein
$R^1$ is selected from the group consisting of H, alkyl, alkylaryl, alkyl-heteroaryl, alkyl-cycloalkyl and alkyl-cycloheteroalkyl;
$R^2$ is selected from the group consisting of H and lower alkyl; and
$R^3$ is selected from the group consisting of H, lower alkyl, aryl, lower alkyl aryl and aryloxyalkyl.

According to another aspect of the present invention there is provided a method for treating ocular hypertension by administering to a subject in need of such a treatment an effective amount of an ophthalmic pharmaceutical composition containing a succinimide compound of formula II as the active ingredient:

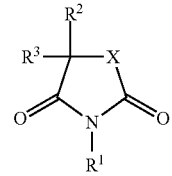

wherein X is —O— or —$CHR^4$,
$R^1$ is selected from the group consisting of H, alkyl, alkylaryl, alkyl-heteroaryl, alkyl-cycloalkyl and alkyl-cycloheteroalkyl;
$R^2$ is selected from the group consisting of H and lower alkyl;
$R^3$ and $R^4$ are independently selected from the group consisting of H, lower alkyl, aryl, lower alkyl aryl and aryloxyalkyl.

In some embodiments, the succinimide compound of formula I or II is an anti-epileptic agent. In other embodiments, the succinimide compound of formula I or II is an anti-convulsant agent. Each possibility represents a separate embodiment of the present invention.

According to another aspect of the present invention there is provided a method for reducing ocular hypertension by administering to a subject in need of such a treatment an effective amount of an ophthalmic pharmaceutical composition containing a succinimide derivative as the active ingredient, wherein the succinimide derivative is a compound of structure I. According to another aspect of the present invention there is provided a method for reducing ocular hypertension by administering to a subject in need of such a treatment an effective amount of an ophthalmic pharmaceutical composition containing a succinimide derivative as the active ingredient, wherein the succinimide derivative is a compound of structure II.

In one preferred embodiment of formula I or II, $R^1$ is H, alkyl or alkyl-cycloheteroalkyl. In another preferred embodiment of formula I or II, $R^1$ is H, methyl or methylmorpholine. In another preferred embodiment of formula I or II, $R^2$ is H, methyl or ethyl. In another preferred embodiment of formula I or II, $R^3$ is lower alkyl or aryl. In another preferred embodiment of formula I or II, $R^3$ is methyl or phenyl.

In some embodiments, the ocular hypertension is associated with glaucoma. In another embodiment, the succinimide compound is an anti-epileptic agent or an anti-convulsant agent, which is preferably active against absence seizures or Petit Mal seizures.

Representative examples of succinimide derivatives that are anti-epileptic or anti-convulsant agents and can also be used to treat ocular hypertension in accordance with the present invention include ethosuximide, methsuximide, phensuximide and morsuximide.

Preferably the pharmaceutical composition is administered topically to the eye of the subject, preferably in the form of an eye drop solution, an ointment, a suspension, a gel or a cream. However, administration can also be local or systemic. In one embodiment, the pharmaceutical composition is applied in 1 to 4 doses a day wherein each dose contains about 1 to about 1,000 mg, preferably from about 10 to about 500 mg of the succinimide derivative of formula I or II. The concentration of the succinimide compound in the pharmaceutical composition can vary, but is typically in the range of about 1 to about 5,000 mg/ml, preferably from about 50 to about 2,500 mg/ml. In another embodiment, the pharmaceutical composition is administered by means of a drug-delivery device inserted into the eye of the subject.

Another aspect of the invention is a topical ophthalmic pharmaceutical composition for the treatment of glaucoma comprising a succinimide derivative as an active agent and a carrier suitable for topical delivery. The topical pharmaceutical compositions of the invention may be formulated as a solution, a suspension, a gel or an emulsion to be applied as eye-drops or as an ointment, and may contain, besides the active ingredient and the carrier, other pharmaceutically acceptable agents and excipients, such as such as stabilizers, preservatives, chelating agents, viscosity modifying agents, buffering agents and/or pH adjusting agents. Additionally, the compositions may contain one or more other ophthalmic active agents such as antibacterial agents, comfort enhancers, antioxidants, additional intra-ocular pressure (IOP) reducing drugs, and the like. The compositions may further contain controlled, sustained, delayed or extended release means.

A further aspect of the invention relates to the use of a succinimide derivative of formula I or II in the manufacture of an ophthalmic pharmaceutical composition for the treatment of ocular hypertension such as glaucoma.

Further embodiments and the full scope of applicability of the present invention will become apparent from the detailed description given hereinafter. However, it should be understood that the detailed description and representative examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The present invention provides methods and ophthalmic pharmaceutical compositions for treating ocular disorders associated with elevated intraocular pressure, such as glaucoma, which are based on a novel use of anti-epileptic or anti-convulsant compounds of the succinimide family, in particular compounds of formula I and/or II, as well as representative examples of compounds encompassed by such formulae, as ocular hypotensive agents.

The succinimide ring continues to be incorporated into many new compounds with diverse applications. In the pharmaceutical field alone, succinimide-derived drugs have recently been evaluated as anti-tumor agents, oxytocin antagonists, anti-HIV drugs, anti-anxiety agents, analgesics and aldose reductase inhibitors (Rankin G. O.: Nephrotoxicity induced by C- and N-Arylsuccinimides. J. Toxicol. Envirom. Health, Part B, 7:399-416, 2004). The present invention focuses on the anti-glaucoma properties of succinimides, in particular succinimides that exhibit antiepileptic and/or anti-seizure activity and more particularly succinimides that are useful for absence seizures, i.e., compounds of formula I or II, including but not limited to known anti-epileptic or anti-convulsant agents such as ethosuximide, phensuximide, methsuximide and morsuximide. In addition, to the aforementioned compounds, other succinimides that have anti-epileptic activity or anti-convulsant activity are also encompassed by the present invention. In accordance with the present invention, it is proposed for the first time that the antiepileptic medications of the succinimide type, in particular compounds of formula I or II, such as ethosuximide, phensuximide, methsuximide and morsuximide, have ocular hypotensive efficacy, possibly by modulating the ionic channels, controlling the rate of production and secretion of the aqueous humor from the non-pigmented ciliary body of the eye. Accordingly, the present invention provides a novel use of succinimide anti-epileptic or anti-convulsant drugs, in particular compounds of formula I or II, for the treatment of ocular disorders associated with elevated ocular pressure and of glaucomas in particular.

In some embodiments, the succinimide-derived compounds of the invention are of formula I:

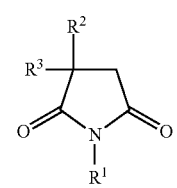

I where $R^1$ is selected from the group consisting of H, alkyl, alkylaryl, alkyl-heteroaryl, alkyl-cycloalkyl and alkyl-cycloheteroalkyl; and $R^2$ and $R^3$ are independently selected from the group consisting of H, lower alkyl, aryl, aryl lower alkyl and aryloxyalkyl.

In some embodiments, the compounds of formula I are those wherein $R^1$ is selected from the group consisting of H, alkyl, alkylaryl, alkyl-heteroaryl, alkyl-cycloalkyl and alkyl-cycloheteroalkyl; $R^2$ is selected from the group consisting of H and lower alkyl; and $R^3$ is selected from the group consisting of H, lower alkyl, aryl, lower alkyl aryl and aryloxyalkyl.

In some embodiments, the succinimide-derived compounds of the invention are of formula II:

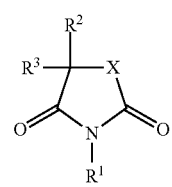

II wherein X is —O— or —CHR⁴, $R^1$ is selected from the group consisting of H, alkyl, alkylaryl, alkyl-heteroaryl, alkyl-cycloalkyl and alkyl-cycloheteroalkyl; and $R^2$ and $R^3$ and $R^4$ are independently selected from the group consisting of H, lower alkyl, aryl, aryl lower alkyl and aryloxyalkyl. When X is an oxygen atom, the compounds are known as oxazolidinedione derivatives.

In some embodiments, the compounds of formula II are those wherein X is —O— or —CHR⁴; $R^1$ is selected from the group consisting of H, alkyl, alkylaryl, alkyl-heteroaryl, alkyl-cycloalkyl and alkyl-cycloheteroalkyl; $R^2$ is selected from the group consisting of H and lower alkyl; and $R^3$ and $R^4$ are independently selected from the group consisting of H, lower alkyl, aryl, lower alkyl aryl and aryloxyalkyl.

Representative examples of succinimide derivatives of structure I already in use as antiepileptic drugs are ethosuximide ($R^1$=H, $R^2$=ethyl, $R^3$=methyl), phensuximide ($R^1$=methyl, $R^2$=H, $R^3$=phenyl); methosuximide ($R^1$=methyl, $R^2$=methyl, $R^3$=phenyl); and morsuximide ($R^1$=methylmorpholine, $R^2$=H, $R^3$=phenyl). Other succinimide derivatives of formula I were also found to exhibit anti-seizure activity. For example, U.S. Pat. No. 4,188,398 teaches antiepileptic activity of □-/para-isopropyloxyphenyl/succinimides ($R^1$=H, $R^2$=H, $R^3$=phenyloxyisopropyl). U.S. Pat. No. 4,981,867 discloses the use of succinimides of formula II for reducing tremor. The contents of the aforementioned patents are incorporated by reference in their entirety as if fully set forth herein.

Chemical Definitions:

The term "lower alkyl" as used herein denotes a "$C_1$ to $C_5$ alkyl" or "$C_{1-5}$ alkyl", which terms are used herein interchangeably. A "$C_1$ to $C_5$ alkyl" or "$C_{1-5}$ alkyl" as used herein alone or as part of another group denotes a linear and branched, saturated alkyl group containing 1 to 5 carbon atoms. Examples of saturated alkyl groups include but are not limited to methyl, ethyl, n-propyl, isopropyl, n-butyl, isobutyl, sec-butyl, tert-butyl, 1-pentyl, 2-pentyl, and 3-pentyl. Similarly, the term "$C_1$ to $C_5$ alkylene" or "$C_{1-5}$ alkylene" denotes a bivalent radical of 1 to 5 carbons.

The $C_1$ to $C_5$ alkyl group can be unsubstituted, or substituted with one or more substituents selected from the group consisting of halogen, hydroxy, alkoxy, aryloxy, alkylaryloxy, heteroaryloxy, oxo, cycloalkyl, phenyl, heteroaryl, heterocyclyl, naphthyl, amino, alkylamino, arylamino, heteroarylamino, dialkylamino, diarylamino, alkylarylamino, alkylheteroarylamino, arylheteroarylamino, acyl, acyloxy, nitro, carboxy, carbamoyl, carboxamide, cyano, sulfonyl, sulfonylamino, sulfinyl, sulfinylamino, thiol, $C_1$ to $C_{10}$ alkylthio, arylthio, or $C_1$ to $C_{10}$ alkylsulfonyl groups. Any substituent can be unsubstituted or further substituted with any one of these aforementioned substituents.

The term "cycloalkyl" used herein alone or as part of another group denotes a $C_3$ to $C_8$ cycloalkyl which alone or as part of another group denotes any saturated monocyclic or polycyclic group. Nonlimiting examples of cycloalkyl groups are cyclopropyl, cyclobutyl, cyclopentyl, cyclohexyl or cycloheptyl. The cycloalkyl group can be unsubstituted or substituted with any one or more of the substituents defined above for alkyl. Similarly, the term "cycloalkylene" means a bivalent cycloalkyl, as defined above, where the cycloalkyl radical is bonded at two positions connecting together two separate additional groups.

The term "aryl" used herein alone or as part of another group denotes an aromatic ring system containing from 6-14 ring carbon atoms. The aryl ring can be a monocyclic, bicyclic, tricyclic and the like. Non-limiting examples of aryl groups are phenyl, naphthyl including 1-naphthyl and 2-naphthyl, and the like. The aryl group can be unsubstituted or substituted through available carbon atoms with one or more groups defined hereinabove for alkyl.

The term "heteroaryl" as used herein alone or as part of another group a heteroaromatic system containing at least one heteroatom ring atom selected from nitrogen, sulfur and oxygen. The heteroaryl generally contains 5 or more ring atoms. The heteroaryl group can be monocyclic, bicyclic, tricyclic and the like. Also included in this expression are the benzoheterocyclic rings. If nitrogen is a ring atom, the present invention also contemplates the N-oxides of the nitrogen containing heteroaryls. Nonlimiting examples of heteroaryls include thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolyl, quinolyl, naphthyridinyl, quinoxalinyl, quinazolinyl, cinnolinyl, pteridinyl, carbolinyl, thiazolyl, oxazolyl, isothiazolyl, isoxazolyl and the like. The heteroaryl group can optionally be substituted through available atoms with one or more groups defined hereinabove for alkyl. The heteroaryl group can be unsubstituted or substituted through available atoms with one or more groups defined hereinabove for alkyl.

The terms "cycloheteroalkyl" or "heterocyclic ring" or "heterocyclyl" used herein interchangeably alone or as part of another group denotes a five-membered to eight-membered rings that have 1 to 4 heteroatoms, such as oxygen, sulfur and/or nitrogen, in particular nitrogen, either alone or in conjunction with sulfur or oxygen ring atoms. These five-membered to eight-membered rings can be saturated, fully unsaturated or partially unsaturated, with fully saturated rings being preferred. Preferred heterocyclic rings include piperidinyl, piperidinyl, pyrrolidinyl pyrrolinyl, pyrazolinyl, pyrazolidinyl, piperidinyl, morpholinyl, thiomorpholinyl, pyranyl, thiopyranyl, piperazinyl, indolinyl, dihydrofuranyl, tetrahydrofuranyl, dihydrothiophenyl, tetrahydrothiophenyl, dihydropyranyl, tetrahydropyranyl, and the like. The heterocyclyl group can be unsubstituted or substituted through available atoms with one or more groups defined hereinabove for alkyl.

The term "alkylaryl" as used herein alone or as part of another group denotes an alkyl group as defined herein, attached to an aryl group as defined herein. The alkylaryl group can be unsubstituted or substituted through available carbon atoms with one or more groups defined hereinabove for alkyl.

The term "alkyl-heteroaryl" as used herein alone or as part of another group denotes an alkyl group as defined herein, attached to a heteroaryl group as defined herein. The alkyl-heteroaryl group can be unsubstituted or substituted through available carbon atoms with one or more groups defined hereinabove for alkyl.

The term "alkyl-cycloalkyl" as used herein alone or as part of another group denotes an alkyl group as defined herein, attached to a cycloalkyl group as defined herein. The alkyl-cycloalkyl group can be unsubstituted or substituted through available carbon atoms with one or more groups defined hereinabove for alkyl.

The term "alkyl-cycloheteroalkyl" as used herein alone or as part of another group denotes an alkyl group as defined herein, attached to a cycloheteroalkyl group as defined herein. The alkyl-cycloheteroalkyl group can be unsubstituted or substituted through available carbon atoms with one or more groups defined hereinabove for alkyl.

Pharmaceutical Compositions and Therapeutic Uses

In some embodiments, the present invention provides a method for treating disorders associated with elevated intraocular pressure, and in particular for treating glaucoma, by administering an effective amount of ophthalmic pharmaceutical compositions comprising a succinimide-derived compound of formula I and/or II as the active ingredient and a pharmaceutically acceptable carrier.

In other embodiments, the present invention provides a method for treating elevated intraocular pressure, and in particular for treating glaucoma, by administering an effective amount of ophthalmic pharmaceutical compositions comprising a succinimide-derived compound of formula I and/or II as the active ingredient and a pharmaceutically acceptable carrier.

In other embodiments, the present invention provides a method for treating glaucoma, by administering an effective amount of ophthalmic pharmaceutical compositions comprising a succinimide-derived compound of formula I and/or II as the active ingredient and a pharmaceutically acceptable carrier.

In particular embodiments, the succinimide derivative is selected from the group consisting of ethosuximide, phensuximide, methosuximide and morsuximide.

Preferably, the pharmaceutical compositions of the invention are administered topically onto the eye of a patient for facilitating effective intraocular levels of the drug and for preventing unnecessary drug level in other organs. Such a non-systemic, site-specific administration reduces the side effects associated with the drugs. However, oral or otherwise systemic administration in a dosage effective for reducing the intraocular pressure is also possible. For example, the composition may be administered by a dermal patch for extended release.

When administration is topical, the pharmaceutical compositions if containing the succinimide derivative may be formulated in various therapeutic forms suitable for topical delivery, including solutions, suspensions, emulsions and gels. The carrier in these formulations may be any pharmaceutical acceptable carrier such as saline, buffered saline, carbopol gel, mineral oil and the like. The formulations can be prepared in accordance with known procedures for the preparation of ophthalmic formulations. Preferably, the concentration of the succinimide derivative in the pharmaceutical compositions is in the range of about 1 to about 5,000 mg/ml, preferably from about 50 to about 2,500 mg/ml and the formulation is preferably applied in one to four doses wherein each dose contains about 1 to 1,000 mg of the succinimide compound, more preferably from about 10 to about 500 mg of succinimide compound.

The topical pharmaceutical compositions may be in the form of eye-drops to be applied by instillation into the eye or may be in the form of a viscous ointment, gel or cream to be applied by an ointment onto the ocular surface and may contain control release means for facilitating sustained release over a prolonged period of time.

The compositions may further include non-toxic auxiliary pharmaceutically acceptable substances such as stabilizers, preservatives, chelating agents, viscosity modifying agents, buffering agents and/or pH adjusting agents. Additionally, the compositions may contain other ophthalmic active agents such as antibacterial agents, comfort enhancers, antioxidants, intra-ocular pressure (IOP)-reducing drugs and the like.

In accordance with other embodiments, the succinimide compound may be loaded into a drug-delivery device to be inserted or implanted into the eye of the patient for allowing releasing of the drug in a controlled and continuous rate, by dissolving, diffusion or leaching, thus maintaining effective therapeutic concentration over a prolonged period of time. The drug-delivery device may be for example a biocompatible thin film loaded with the active agent, inserted for example beneath the lower eyelid.

EXAMPLES

Example 1

Effect of Ethosuximide on the Intraocular Pressure in Rats

Preliminary ocular pharmacodynamic studies were conducted to study the effect of ethosuximide on the intraocular pressure in rats by measuring IOP before and after administration of ethosuximide. IOP measurements were taken by a tonopen instrument. Ethosuximide was applied as a viscous solution obtained from Petnidan® capsules (Desitin, Hamburg, Germany). A recent study at Alcon Research laboratory (Pang I H, Wang W H, Clark A F: Acute effects of glaucoma medications on rat intraocular pressure, *Exp Eye Res* 2005, February; 80(2)207-14) has shown rats to be a proper animal model for glaucoma study. Another study at the Casey Eye Institute (Moore C G, Milne S T, Morrison J C: Noninvasive measurements of rat intraocular pressure with the Tono-Pen. Invest. *Opthalmol. Vis. Sci.* 1993 February; 34(2)363-9) has shown that a tonopen can be used reliably to measure IOP in normal rat eye.

Six Dark Agauti (DA) pigmented rats, (250-300 g in weight) were slightly sedated with 1.5-2 mg (0.15-0.2 ml) of intraperitoneal xylazine. One eye of each rat was randomly selected to receive topical administration of 50 □l of 250 mg/0.2 ml ethosuximide solution (content of Petnidan capsules). The second (control) eye received 50 □l of viscoelastic solution without the active ingredient (Viscotears™ manufactured by Novartis, Switzerland). At t=0 (immediately before) and at 30, 60 and 120 minutes after administration, topical anesthetic benoxinate was applied to both eyes and the intraocular pressures (IOP) were measured by a Tono-Pen XL tonometer (Medtronics). IOP values were recorded as the mean value of 6-10 successive measurements to minimize variability. The code, namely which eye of a pair was treated, was unknown to the technician who performed the IOP measurements. One rat expired after 1 hour due to excessive sedation. Five rats completed the experiment. In 2 out of 6 eyes that received the drug (vs. 1 of 6 eyes that were administered viscoelastic vehicle) a mild to moderate limbal vascular congestion was noticed, which tended to subside at 60 minutes.

At the end of the experiment, the code was broken and the IOP values in control and treated eyes were compared by statistical analysis. The results are summarized in following Table 1.

TABLE 1

IOP values (mmHg) measured in rats before (t = 0) and at 30, 60 and 120 minutes after administration of ethosuximide solution: T = treated eye; or vehicle only: C = control eye.

| | Time | | | | | | | |
|---|---|---|---|---|---|---|---|---|
| | 0 | | 30 min | | 60 min | | 120 min | |
| | eye | | | | | | | |
| | C | T | C | T | C | T | C | T |
| Rat #1 | 15 | 15.5 | 13 | 17 | 20.3 | 21.3 | 32.5 | 22 |
| Rat #2 | 13 | 17 | 13.5 | 16 | 30 | 30 | 17 | 17 |
| Rat #3 | 22 | 22 | 19 | 15 | 20.3 | 18 | 20.5 | 19 |
| Rat #4 | 23 | 25 | 19 | 15.3 | 16 | 14.6 | 20 | 20.5 |

TABLE 1-continued

IOP values (mmHg) measured in rats before (t = 0) and
at 30, 60 and 120 minutes after administration of ethosuximide
solution: T = treated eye; or vehicle only: C = control eye.

|  | Time | | | | | | | |
|---|---|---|---|---|---|---|---|---|
|  | 0 | | 30 min | | 60 min | | 120 min | |
|  | eye | | | | | | | |
|  | C | T | C | T | C | T | C | T |
| Rat #5 | 15 | 18 | 18 | 20.5 | 20.3 | 21.3 | 19.7 | 20.2 |
| Rat #6 | 20 | 24 | 26 | 22 | — | — | — | — |
| Total | 108 | 121.5 | 108.5 | 105.8 | 106.9 | 105.2 | 111.6 | 98.7 |
| Average $\overline{X}$ | 18 | 20.2 | 18.1 | 17.6 | 21.4 | 21.0 | 22.3 | 19.7 |
| Δ (IOP) C - T | | −2.2 | | +0.5 (p > 0.05) | | +0.4 (p > 0.05) | | +2.6 (p < 0.05) |

As can be seen in Table 1, at 30 and 60 minutes after administration, a modest decrease in the IOP was depicted, (0.5 mmHg and 0.4 mmHg respectively), which was not significant either clinically or statistically. However, at 120 minutes, a decrease of 2.6 mmHg was noticed in the treated eyes versus control. This clinically significant effect was also statistically significant (p<0.05, using two-tailed Student's t-test for paired data). It was also statistically significant when using ANOVA analysis.

The results of the preliminary study clearly indicate the potential of ethosuximide and other succinimide derivatives as ocular hypotensive agents and their use in the preparation of anti glaucoma drugs, in particular in the preparation of ophthalmic pharmaceutical compositions for topical administration.

Example 2

Effect of Ethosuximide on the Intraocular Pressure in Rabbits

Another study was conducted, in order to study the effect of ethosuximide on the intraocular pressure in rabbits by measuring IOP before and after administration of ethosuximide. IOP measurements were taken by a tonopen instrument. Ethosuximide was applied as a viscous solution obtained from Petnidan® capsules (Desitin, Hamburg, Germany).

Five fully awake, normo-tensive New Zealand White (NZW) rabbits, (each approximately 3.0 kg in weight) were used in this study. One eye of each rabbit was randomly selected to receive topical administration of 50 μl of 250 mg/0.2 ml ethosuximide solution (content of Petnidan capsules). The second (control) eye received 50 μl of viscoelastic solution without the active ingredient (Viscotears™ manufactured by Novartis, Switzerland). At t=0 (baseline, immediately before) and at 0.5, 1, 2, 4 and 6 hours after administration, topical anesthetic benoxinate was applied to both eyes and the intraocular pressures were measured by a Tono-Pen XL tonometer (Medtronics). IOP values were recorded as the mean value of 6-10 successive measurements to minimize variability. The code, namely which eye of a pair was treated, was unknown to the technician who performed the IOP measurements. In 3 out of 5 eyes that received the drug (vs. 1 of 5 eyes that were administered viscoelastic vehicle) a mild to moderate limbal vascular congestion was noticed, which tended to subside at 60 minutes. In one treated eye the congestion persisted for two hours. At the end of the experiment, the code was broken and the IOP values in control and treated eyes were compared. The results are summarized in Table 2.

TABLE 2

IOP values (mmHg) measured in NZW rabbits before (t = 0) and at 0.5, 1, 2, 4 and 6 hours
after administration of ethosuximide solution: T = treated eye; or vehicle only: C = control eye.

|  | Time (hour) | | | | | | | | | | | |
|---|---|---|---|---|---|---|---|---|---|---|---|---|
|  | 0 | | 0.5 | | 1 | | 2 | | 4 | | 6 | |
|  | Eye | | | | | | | | | | | |
|  | C | T | C | T | C | T | C | T | C | T | C | T |
| NZW#1 | 25.8 | 26.8 | 23.0 | 20.0 | 22.3 | 18.5 | 22.3 | 19.8 | 20.2 | 17.5 | 18.5 | 16.0 |
| NZW#2 | 19.8 | 19.8 | 20.3 | 17.3 | 14.0 | 12.8 | 19.8 | 17.3 | 20.8 | 15.5 | 17.0 | 19.5 |
| NZW#3 | 20.0 | 18.8 | 17.8 | 18.3 | 16.6 | 16.0 | 20.5 | 20.0 | 21.0 | 15.8 | 18.8 | 20.0 |
| NZW#4 | 15.5 | 18.3 | 15.2 | 16.3 | 15.0 | 15.0 | 18.0 | 19.6 | 14.0 | 13.0 | 15.0 | 13.5 |
| NZW#5 | 19.5 | 16.3 | 21.0 | 19.7 | 17.3 | 19.7 | 19.3 | 16.3 | 15.8 | 12.5 | 18.6 | 19.4 |
| Mean | 20.1 | 20.0 | 19.5 | 18.3 | 16.6 | 16.0 | 20.0 | 18.6 | 18.4 | 14.9 | 17.6 | 17.7 |
| SD± | 3.7 | 3.9 | 3.0 | 1.6 | 3.9 | 2.8 | 1.6 | 1.7 | 3.2 | 2.0 | 1.6 | 2.8 |
| Δ IOP* vs t = o** | −0.1 | — | −1.2 | −1.7 | −0.6 | −3.9 | −1.4 | −1.4 | −3.5 | −5.1 | +0.1 | −2.3 |
| p (t-test) Vs t = o*** | .911 | — | .254 | .365 | .557 | .153 | .184 | .420 | .012 | 0.01 | .920 | .404 |

*= difference in mean IOP (T − C) at each time point; in mmHg
**= difference between mean IOP of the treatment groups at each time points versus t = o, in mmHg
***= P value among treatment groups: t = ½, 1, 2, 4, and 6 hours vs. t = o (ANOVA)

As can be seen in Table 2, at 0.5 and 2 hours after instillation, a modest decrease in the IOP was noticed, of 1.2 and 1.4 mmHg, respectively, which was not statistically significant. However, 4 hours after instillation, a 3.5 mmHg difference in the IOP decrease between the treatment and the control eyes was measured (p=0.012, by two-tailed Student's t-test for paired data).

When the effect in the treated eyes was compared, each time point vs. change from baseline (t=0), a decrease in the IOP was also noticed at ½ and 1 hour post instillation, of 1.7 and 3.9 mmHg, respectively, but this effect did not reach statistical significance, probably due to the small sample size and high variability. Whereas, the maximal effect, measured at 4 hours post instillation, (a decrease of 5.1 mmHg) was statistically significant (p=0.01)

In summary, the results of the studies indicate the potential of ethosuximide as a topical ocular hypotensive agent.

Persons skilled in the art will appreciate that the present invention is not limited to what has been particularly shown and described hereinabove. Rather the scope of the present invention is defined only by the claims, which follow.

What is claimed is:

1. A method for treating or reducing ocular hypertension, comprising the step of administering to a subject in need of such a treatment an effective amount of an ophthalmic pharmaceutical composition comprising a succinimide compound represented by the structure of formula II:

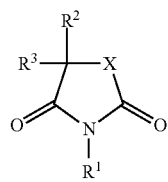

wherein X is —O— or —CHR$^4$,
R$^1$ is selected from the group consisting of H, alkyl, alkylaryl, alkyl-heteroaryl, alkyl-cycloalkyl and alkyl-cycloheteroalkyl;
R$^2$ is selected from the group consisting of H and lower alkyl; and
R$^3$ and R$^4$ are independently selected from the group consisting of H, lower alkyl, aryl, lower alkyl aryl and aryloxyalkyl.

2. The method of claim 1 wherein said ocular hypertension is associated with glaucoma.

3. The method of claim 1 wherein said succinimide compound is an anti-epileptic or an anti-convulsant agent.

4. The method of claim 3 wherein said anti-epileptic or anti-convulsant agent is active against absence seizures or Petit Mal seizures.

5. The method of claim 1, wherein the succinimide compound is represented by the structure of formula I:

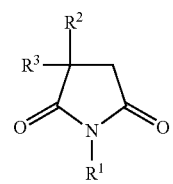

wherein R$^1$, R$^2$ and R$^3$ are as defined in claim 1.

6. The method of claim 5, wherein R$^1$ is H, alkyl or alkyl-cycloheteroalkyl.

7. The method of claim 6, wherein R$^1$ is H, methyl or methylmorpholine.

8. The method of claim 1, wherein R$^2$ is H, methyl or ethyl.

9. The method of claim 1, wherein R$^3$ is lower alkyl or aryl.

10. The method of claim 9, wherein R$^3$ is methyl or phenyl.

11. The method of claim 1 wherein said succinimide compound is selected from the group consisting of ethosuximide, methsuximide, phensuximide and morsuximide.

12. The method of claim 1 wherein said pharmaceutical composition is applied topically to the eye of said subject in the form of an eye-drop solution, an ointment, a suspension, a gel or a cream.

13. The method of claim 1 wherein said pharmaceutical composition is administered by means of a drug-delivery device inserted into the eye of said subject.

14. The method of claim 1 wherein said pharmaceutical composition is administered in combination with at least one additional ophthalmic active agent.

15. The method of claim 14, wherein the additional ophthalmic active agent is an antibacterial agent, a comfort enhancer, an antioxidant or an intra-ocular pressure (IOP)-reducing agent.

16. The method of claim 1 wherein the pharmaceutical composition is administered in 1 to 4 doses a day wherein each dose contains about 1 to about 1,000 mg of the succinimide compound of formula II.

17. The method of claim 1 wherein said ophthalmic pharmaceutical composition contains said succinimide compound of formula II at a concentration of about 1 mg/ml to about 5,000 mg/ml.

* * * * *